United States Patent
Park

(10) Patent No.: US 12,318,565 B2
(45) Date of Patent: Jun. 3, 2025

(54) MICRONEEDLE STAMP DEVICE FOR INJECTING LIQUID MEDICINE

(71) Applicant: AJOU UNIVERSITY INDUSTRY-ACADEMIC COOPERATION FOUNDATION, Suwon-si (KR)

(72) Inventor: In Su Park, Seongnam-si (KR)

(73) Assignee: AJOU UNIVERSITY INDUSTRY-ACADEMIC COOPERATION FOUNDATION, Suwon-si (KR)

(*) Notice: Subject to any disclaimer, the term of this patent is extended or adjusted under 35 U.S.C. 154(b) by 789 days.

(21) Appl. No.: 17/633,426

(22) PCT Filed: Aug. 6, 2020

(86) PCT No.: PCT/KR2020/010400
§ 371 (c)(1),
(2) Date: Feb. 7, 2022

(87) PCT Pub. No.: WO2021/025484
PCT Pub. Date: Feb. 11, 2021

(65) Prior Publication Data
US 2022/0280764 A1    Sep. 8, 2022

(30) Foreign Application Priority Data

Aug. 6, 2019    (KR) .................. 10-2019-0095597

(51) Int. Cl.
*A61M 37/00* (2006.01)
*A61M 5/20* (2006.01)
(Continued)

(52) U.S. Cl.
CPC ...... *A61M 37/0015* (2013.01); *A61M 5/2053* (2013.01); *A61M 5/24* (2013.01);
(Continued)

(58) Field of Classification Search
CPC ....... A61M 2037/0007; A61M 37/0015–2037; A61M 37/0061; A61M 5/24;
(Continued)

(56) References Cited

U.S. PATENT DOCUMENTS

| 2015/0157809 | A1* | 6/2015 | Park | A61M 5/31511 604/173 |
| 2017/0340880 | A1* | 11/2017 | Lee | A61M 37/00 |
| 2018/0264043 | A1* | 9/2018 | Pettine | A61K 35/28 |

FOREIGN PATENT DOCUMENTS

| JP | 6348167 B | | 6/2018 |
| KR | 20110013796 A | * | 2/2011 |

(Continued)

OTHER PUBLICATIONS

English Translation of KR 20160045626 (Year: 2013).*
Translation of KR 20110013796 (Year: 2011).*

*Primary Examiner* — Jenna Zhang
(74) *Attorney, Agent, or Firm* — NSIP Law

(57) ABSTRACT

The present invention provides a microneedle stamp device for injecting liquid medicine; a carboxy cartridge provided in the main body portion; a liquid medicine storage portion provided outside the main body portion and connected to the carboxy cartridge; a needle portion connected to the carboxy cartridge and the liquid medicine storage portion; a power portion provided in the grip; a connection portion configured to connect the carboxy cartridge to the needle portion; and a contact plate provided at the contact end of the main body portion, wherein, when the contact plate comes into contact with the skin of the treatment subject, the contact plate slidingly moves to the inside of the contact end to apply an external force to the power portion to operate the power portion to supply the liquid medicine and the carbon dioxide to the needle portion.

7 Claims, 5 Drawing Sheets

(51) Int. Cl.
*A61M 5/24* (2006.01)
*A61M 5/32* (2006.01)
*A61M 5/00* (2006.01)

(52) U.S. Cl.
CPC ........ *A61M 5/2448* (2013.01); *A61M 5/3298* (2013.01); *A61M 2005/006* (2013.01); *A61M 2037/0007* (2013.01); *A61M 2037/0023* (2013.01); *A61M 2037/003* (2013.01); *A61M 2202/0225* (2013.01); *A61M 2205/8281* (2013.01)

(58) Field of Classification Search
CPC .............. A61M 5/2448; A61M 5/2053; A61M 2005/006; A61M 2202/0225
See application file for complete search history.

(56) References Cited

FOREIGN PATENT DOCUMENTS

| | | | |
|---|---|---|---|
| KR | 20160045626 A | * | 4/2016 |
| KR | 10-1653266 B1 | | 9/2016 |
| KR | 10-1675333 B1 | | 11/2016 |
| KR | 10-1739898 B1 | | 5/2017 |
| KR | 10-1759272 B1 | | 7/2017 |
| WO | WO 02/085444 A1 | | 10/2002 |
| WO | WO 2008/095124 A1 | | 8/2008 |

* cited by examiner

MICRONEEDLE STAMP DEVICE FOR INJECTING LIQUID MEDICINE

CROSS REFERENCE TO RELATED APPLICATIONS

This application is a U.S. National Stage Application of International Application No. PCT/KR2020/010400 filed on Aug. 6, 2020, which claims the benefit under 35 USC 119 (a) and 365(b) of Korean Patent Application No. 10-2019-0095597 filed on Aug. 6, 2019 in the Korean Intellectual Property Office, the disclosure of which is incorporated herein by reference.

TECHNICAL FIELD

The present invention relates to a microneedle stamping device for injecting liquid medicine, and more particularly, to a microneedle stamp device for injecting liquid medicine such that the liquid medicine may be conveniently and directly injected into a dermis of a treatment subject through a plurality of microneedles.

BACKGROUND

Referring to the background art described in Korean Patent No. 10-1608179, a health status of the skin has a large effect on the appearance, and thus, various methods are currently used for skin whitening, wrinkle improvement, moisturizing, elasticity increase, and so on in addition to treatment of skin disease.

The human skin may be divided into an epidermis, a dermis, and a fat layer. The dermis, which occupies the most part of the skin, consists of a papillary layer and a reticular layer. Capillaries and lymphatic vessels are arranged in the papillary layer, and the reticular layer includes collagen, which is a collagen fiber related to wrinkles in the skin, elastin which is an elastic fiber that gives elasticity to the skin, and substrate.

As such, a visual condition of the skin is greatly influenced by a health condition of the dermis, and thus, various methods for improving the condition of the skin are mostly applied to the dermis.

Because the dermis is protected by the epidermis as described above, even when liquid medicine to be delivered to the dermis is applied to the skin, the amount and speed of the liquid medicine reaching the dermis are often significantly reduced.

Accordingly, a method of applying pressure or ultrasonic vibration to the dermis has been proposed such that the liquid medicine applied to the epidermis is rapidly delivered to the dermis. This has advantage of not damaging the epidermis but has disadvantage in that the cost is increased and the volume is increased to provide a means for generating a desired pressure or ultrasonic vibration.

In order to overcome the disadvantage, a through-hole is formed in the epidermis with a microneedle (hereinafter, referred to as a "needle"), a method of delivering liquid medicine to the dermal layer by applying the liquid medicine having a desired effect to the skin is widely used.

For example, Korean Patent No. 10-0921009 (hereinafter, referred to as a "related art 1") discloses that a plurality of needles are installed on a surface of a roller through which liquid medicine flows, and the roller is rotated by coming into contact with the skin such that many through-holes are formed in the epidermis by the needles and at the same time the liquid medicine leaked from the roller is easily delivered to the dermis.

A structure of the roller according to the related art 1 has a disadvantage in that a plurality of needles are rotated by the rollers to form a linear long hole toward a tangential direction of the roller without forming a point-shaped through-hole in the skin.

In addition, there is a disadvantage in that, when viscosity of the liquid medicine flowing out from the roller and applied to the skin is low, a possibility that the liquid medicine randomly flows along the skin is increased, and there is a problem in that, when liquid medicine with relatively strict restrictions on the amount and area to be applied is applied, a possibility that the liquid medicine will be applied beyond an intended range increases.

Therefore, there is a need to propose a method for allowing liquid medicine to be applied only in a desired range when the liquid medicine is intended to be directly delivered to the dermis.

SUMMARY OF INVENTION

Technical Problem

The present invention is to meet the proposal while solving the problems described above, and an object of the present invention is to provide a microneedle stamp device that may inject liquid medicine and carbon dioxide without forming a linear long hole in a dermal of a treatment subject and may easily and directly inject the liquid medicine into the dermis of the treatment subject by using simple physical force and pressure of a carboxy cartridge without using a complex electronic device.

Solution to Problem

In order to achieve the object, the present invention provides a microneedle stamp device for injecting liquid medicine including a main body portion including a grip end gripped by a clinician and a contact end to come into contact with a skin of a treatment subject; a carboxy cartridge provided in the main body portion and storing carbon dioxide to be injected into the skin of the treatment subject; a liquid medicine storage portion provided outside the main body portion and connected to the carboxy cartridge and storing the liquid medicine to be injected into the skin of the treatment subject together with the carbon dioxide supplied from the carboxy cartridge; a needle portion connected to the carboxy cartridge and the liquid medicine storage portion and configured to inject the carbon dioxide and the liquid medicine supplied from the carboxy cartridge and the liquid medicine storage portion into the skin of the treatment subject; a power portion provided in the grip end and configured to be operated by an external force applied from an outside to provide pressure to the carboxy cartridge and the liquid medicine storage portion such that the carbon dioxide stored in the carboxy cartridge and the liquid medicine stored in the liquid medicine storage portion is supplied to the needle portion; a connection portion configured to connect the carboxy cartridge to the needle portion; and a contact plate provided at the contact end of the main body portion and protruding to an outside of the contact end and including the needle portion therein and including a plurality of through-holes through which the needle portion passes and configured to slidingly move to the inside of the contact end when coming into contact with the skin of the treatment subject, wherein, when the contact plate comes into contact with the skin of the treatment subject, the contact plate slidingly moves to the inside of the contact end to apply an external force to the power portion to operate the power portion to supply the liquid medicine and the carbon dioxide to the needle portion.

The microneedle stamp device for injecting liquid medicine according to the present invention may further include a contact plate support portion provided in the main body portion to elastically support the contact plate, the contact plate support portion may include a protrusion provided in an inner side of the contact end and protruding inward from an inner surface of the contact end, and a spring member provided in the contact end and having one end in contact with the inner surface of the contact end and the other end in contact with the contact plate, the protrusion may be located inside the spring member, and a guide protrusion may be provided on a circumferential surface of the contact plate to guide a protrusion range of the contact plate protruding to an outside of the contact plate.

A pressure button for operating the power portion may be exposed to an outside of the power portion, and when the contact plate slidingly moves, the contact plate may press the pressure button to operate the power portion, and the power portion may be formed with a connection hole through which one end of the liquid medicine storage portion passes to be connected to the carboxy cartridge.

The adhesive plate may include a contact member having a plurality of through-holes through which the needle portion passes, and a pressure member protruding to one side of the contact member and configured to press the pressure button while passing through a through-hole formed in the contact end when the contact plate slidingly moves.

The needle portion may include a plurality of microneedles each having one end passing through the plurality of through-holes, and a mounting plate having one side on which the other end of each of the plurality of microneedles is mounted and the other side on which a connection end connected to the connection portion is provided, and a flow path through which the liquid medicine supplied through the connection portion and the connection end flows may be formed in the mounting plate, and the liquid medicine may be supplied to the plurality of microneedles through the flow path.

A fixed end for fixing the mounting plate to an inside of the contact end may be provided on an outer surface of the mounting plate, and a movement long hole through which the fixed end is moved may be formed in the contact member.

The plurality of microneedles may have thickness of 0.25 mm to 0.8 mm and have lengths of 0.2 mm to 3 mm.

Advantageous Effects of Invention

A microneedle stamp device for injecting liquid medicine according to the present invention may directly inject the liquid medicine and carbon dioxide into a dermis of a treatment subject without forming a linear long hole by using a plurality of microneedles and may easily inject a certain amount of liquid medicine and carbon dioxide into the dermis of the treatment subject with a constant pressure by using simple physical force without using a complex electronic device.

BEST MODE FOR INVENTION

Hereinafter, preferred embodiments according to the present invention will be described in detail with reference to the accompanying drawings. Terms or words used in the present specification and claims should not be construed as being limited to their ordinary or dictionary meanings and should be interpreted with meanings and concepts consistent with the technical idea of the present invention, based on the principle that inventors may adequately define concepts of the terms to best describe their invention.

Referring to FIGS. 1 to 5, a microneedle stamp device 1000 for injecting liquid medicine, according to an embodiment of the present invention may include a main body portion 1100, a carboxy cartridge 1200, a liquid medicine storage portion 1300, a needle portion 1400, a power portion 1500, a connection portion 1600, and a contact plate 1700 and may further include a contact plate support portion 1800.

The main body portion 1100 includes a grip end 1120 gripped by a clinician and a contact end 1140 that is provided on one side of the grip end 1120 and is in close contact with the skin of a treatment subject, and it is preferable that the grip end 1120 has one of a cylindrical shape and a rectangular shape that is easily gripped by a clinician and the inside of the grip end 1120 is hollow.

Figure 4:
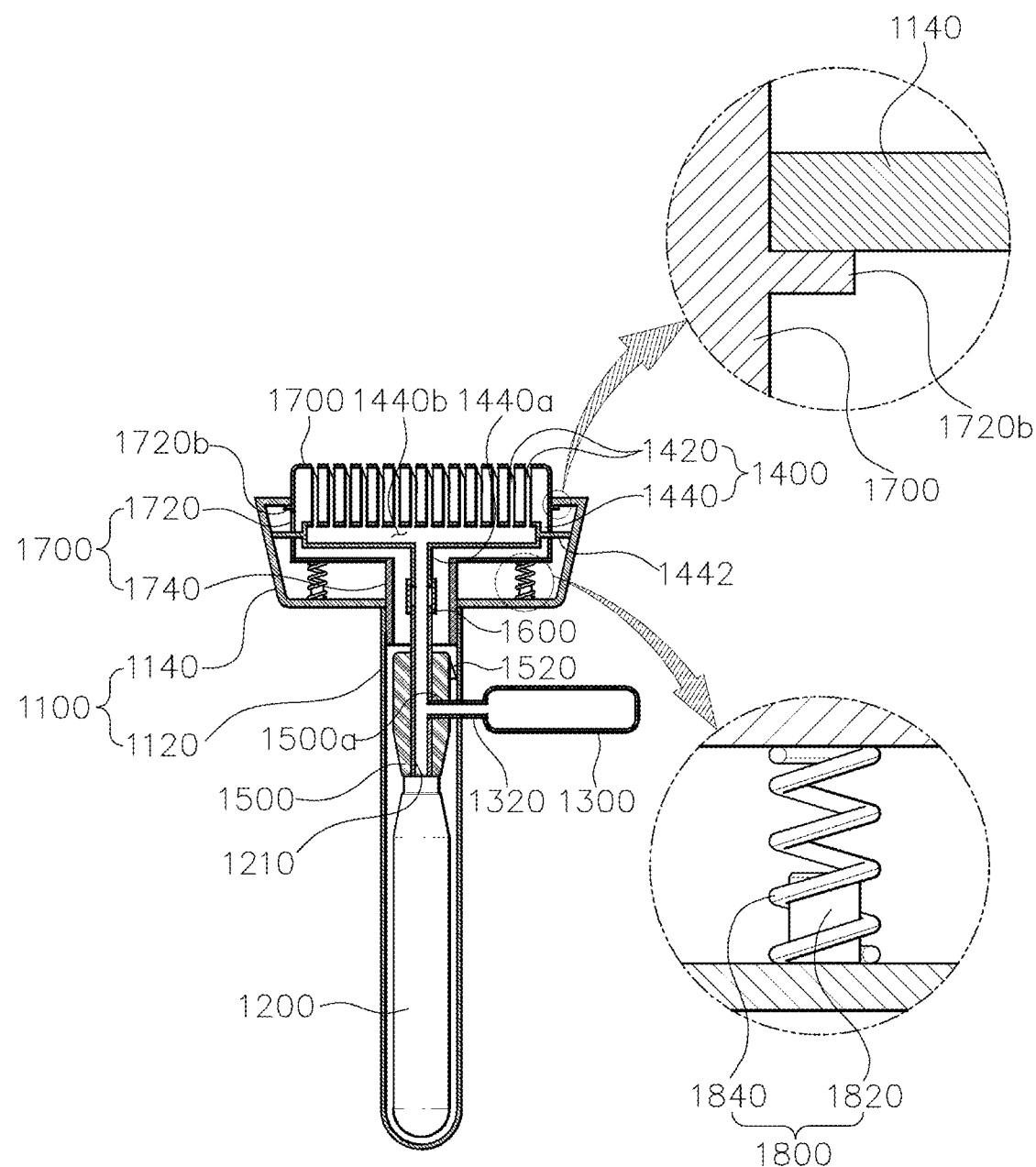
FIG. 4 is a view illustrating an internal state of a main body portion illustrated in FIG. 1.
Figure 5:
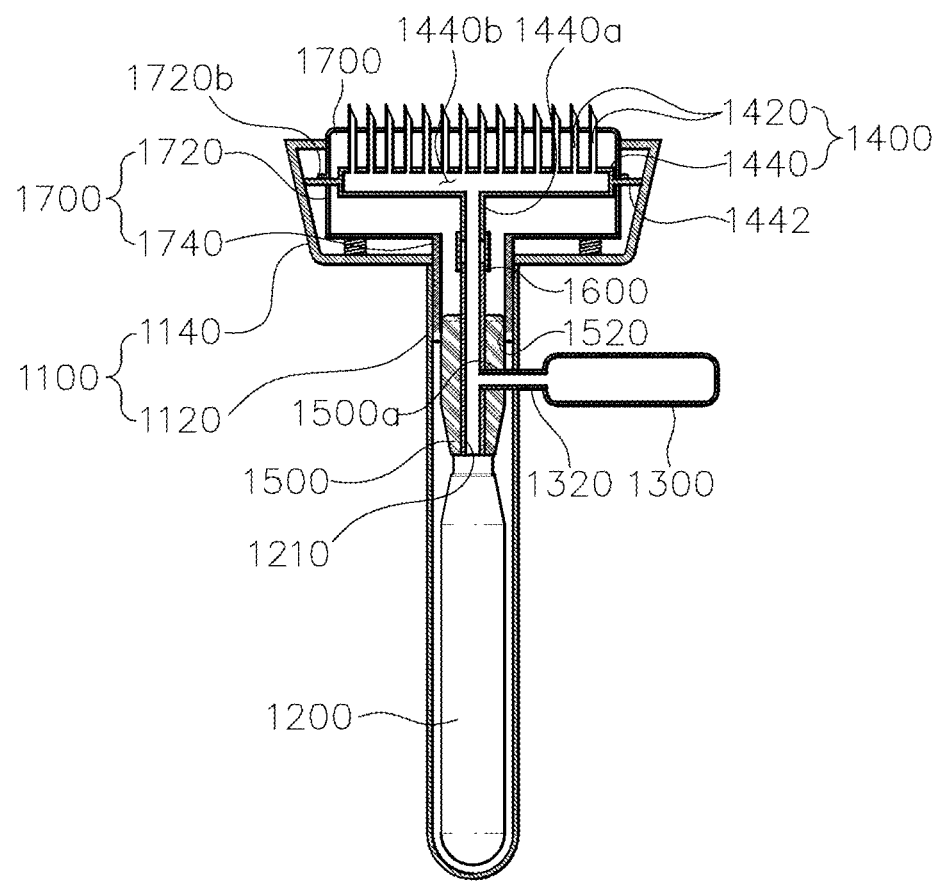
FIG. 5 is a view illustrating a state in which a pressure button is pressed when a contact plate slides.

Referring to FIGS. 4 and 5, the carboxy cartridge 1200 storing carbon dioxide to be injected into a dermis of the skin of a treatment subject together with liquid medicine is provided in the main body portion 1100, and it is preferable that the carbon dioxide to be injected into the dermis of the treatment subject is filled in the carboxy cartridge 1200. The carboxy cartridge 1200 discharges the carbon dioxide filled therein to the outside at a constant pressure and quantity by using pressure provided by the power portion 1500 described below. The carbon dioxide supplied to the dermis of the treatment subject from the carboxy cartridge 1200 cuts off fibroblasts in the dermis and activates an increase in oxygen at an injection site.

It is preferable that the carboxy cartridge 1200 is connected to the liquid medicine storage portion 1300, and the liquid medicine storage portion 1300 is provided in the outside of the main body portion 1100, and one end of the liquid medicine storage portion 1300 is connected to the carboxy cartridge 1200, and liquid medicine to be injected into the skin of the treatment subject together with carbon dioxide supplied from the carboxy cartridge 1200 is stored in the liquid medicine storage portion 1300.

The carboxy cartridge 1200 and the liquid medicine storage portion 1300 are connected to the needle portion 1400, and the needle portion 1400 injects carbon dioxide and liquid medicine supplied from the carboxy cartridge 1200 and the liquid medicine storage portion 1300 into the skin of a treatment subject, preferably into a dermis of the treatment subject.

The needle portion 1400 includes a plurality of microneedles 1420 and a mounting plate 1440 on which the plurality of microneedles 1420 are mounted. One end of each of the plurality of microneedles 1420 is inserted into a dermis of a treatment subject through the contact plate 1700 described below, and it is preferable that flow paths through which liquid medicine and carbon dioxide flow are formed in the plurality of microneedles 1420 to penetrate the plurality of microneedles 1420.

The other end of each of the plurality of microneedles 1420 is mounted on the mounting plate 1440, and the mounting plate 1440 is provided with a connection end 1440a connected to the connection portion 1600 described below, and the connection end 1440a is preferably provided at a position corresponding to the plurality of microneedles 1420.

A flow path 1440b through which liquid medicine and carbon dioxide supplied through the connection portion 1600 and the connection end 1440a described below flow is formed in the mounting plate 1440, and the flow path 1440b is preferably communicate with the flow paths penetrating the microneedles 1420. As the flow path 1440b communicates with the flow paths penetrating the microneedles 1420, liquid medicine and carbon dioxide supplied to the flow path 1440b are directly injected into a dermis of a treatment subject through the microneedles 1420.

The plurality of microneedles 1420 have thicknesses of 0.25 mm to 0.8 mm, and preferably lengths of 0.2 mm to 3 mm. Because the microneedles 1420 have the thicknesses of 0.25 mm to 0.8 mm, small dot-shaped through-holes may be formed in the skin of a treatment subject, and thus, it is possible to prevent contaminants from entering the skin through the through-holes, and because the microneedles have lengths of 0.2 mm to 3 mm, it is possible to prevent contaminants from being injected beyond a dermal layer of the treatment subject.

The carboxy cartridge 1200 is connected to the needle portion 1400 by the connection portion 1600, and the power portion 1500 for providing pressure to the carboxy cartridge 1200 is provided around a connection end 1210 that protrudes from a front end of the carboxy cartridge 1200 and is connected to the connection portion 1600 described below.

The carboxy cartridge 1200 provided in the grip end 1120 is connected to the connection portion 1600 through the power portion 1500, and the carboxy cartridge 1200 is fixed to the inside of the grip end 1120 by using a separate fixed member so as not to move.

The power portion 1500 applies pressure to the carboxy cartridge 1200 and the liquid medicine storage portion 1300 while being operated by an external force applied from the outside, and the liquid medicine and carbon dioxide filled in the carboxy cartridge 1200 and the liquid medicine storage portion 1300 are supplied to the needle portion 1400 through the connection portion 1600 while being discharged to the outside thereof by the pressure supplied from the power portion 1500.

Referring to FIGS. 1, 2, 4, and 5, the power portion 1500 includes a pressure button 1520 that operates the power portion 1500 and is exposed to the outside, and the power portion 1500 operates when the pressure button 1520 is pressed while the contact plate 1700 described below slidingly moves. The power portion 1500 is preferably formed with a connection hole 1500a through which a connection conduit 1320 protruding from one side of the liquid medicine storage portion 1300 passes to be connected to the connection end 1210 of the carboxy cartridge 1200.

the contact plate 1700 is provided on the contact end 1140 of the main body portion 1100 and is exposed to the outside of the contact end 1140. The contact plate 1700 includes a contact member 1720 having a plurality of through-holes 1720a through which the needle portion 1400 passes, and a pressure member 1740 that protrudes from one side of the contact member 1720 and presses the pressure button 1520 when the contact plate 1700 slidingly moves.

The pressure member 1740 presses the pressure button 1520 while passing through a through-hole 1140a formed in the inside of the contact end 1140 when the contact plate 1700 slidingly moves.

Figure 1:
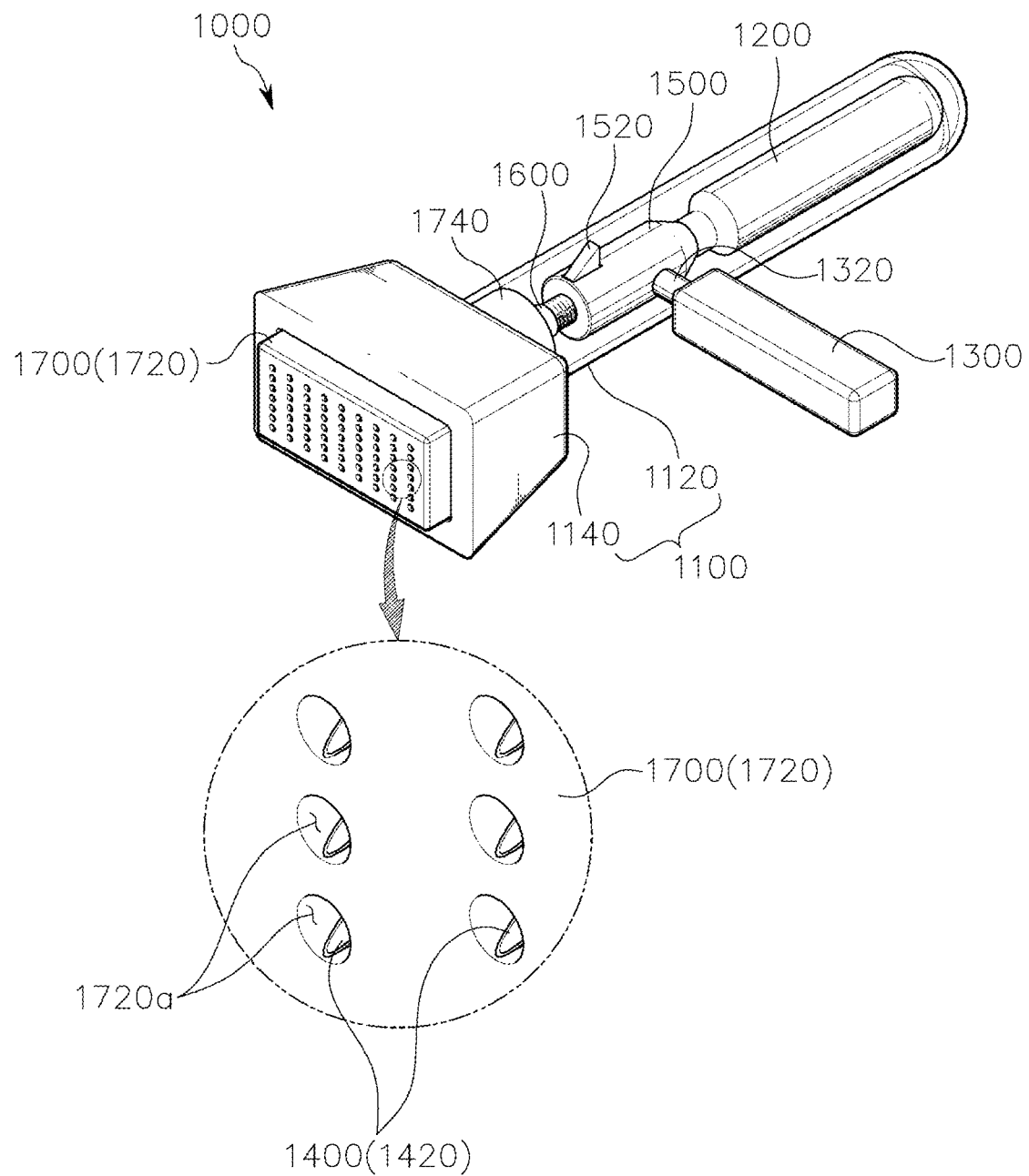
FIG. 1 is a schematic view illustrating a microneedle stamp device for injecting liquid medicine, according to an embodiment of the present invention.
Figure 2:
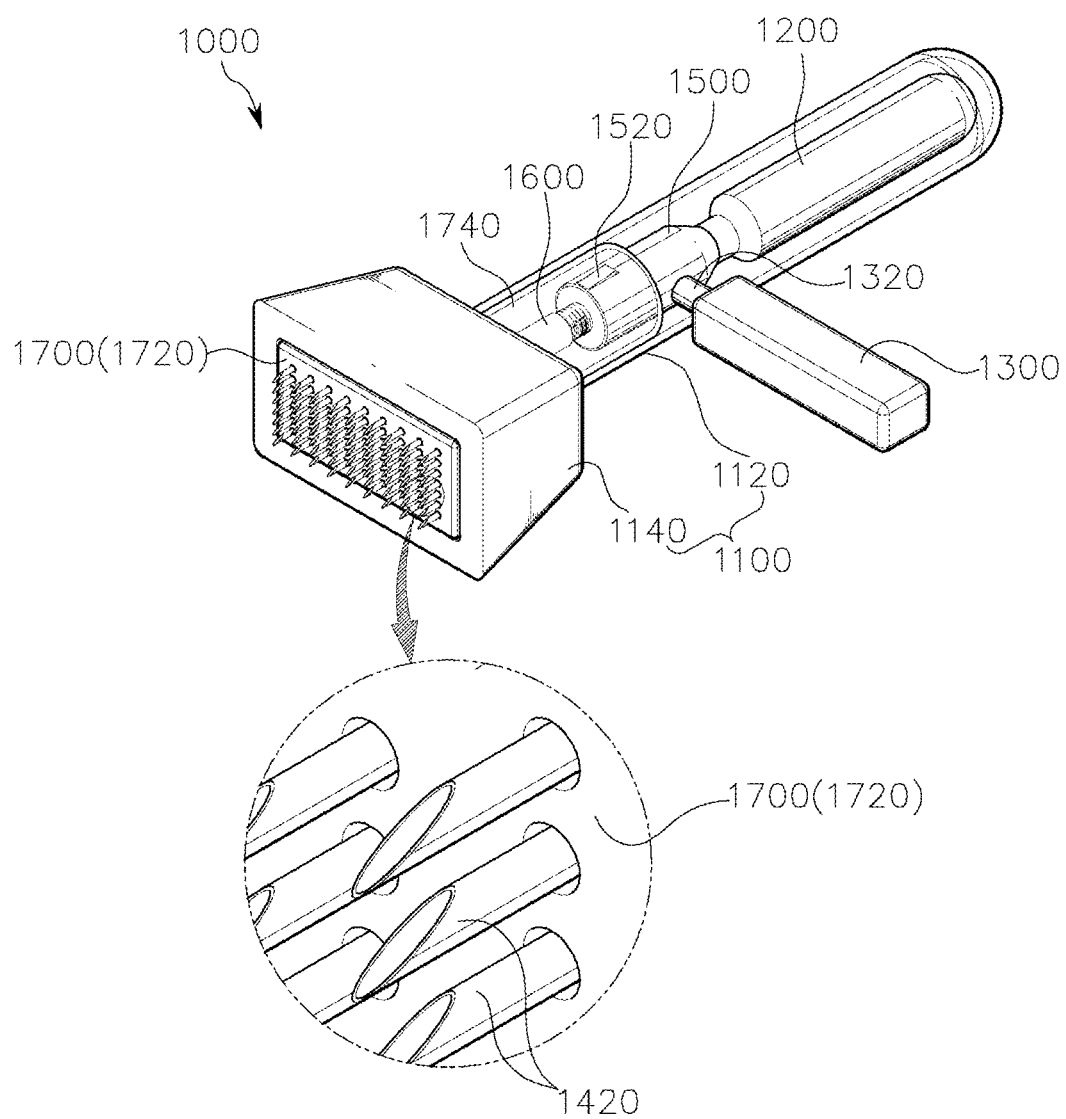
FIG. 2 is a view illustrating a state in which a microneedle of a needle portion is exposed to the outside of a contact plate while the contact plate illustrated in FIG. 1 is pushed and a state in which a pressing button of a power portion is pressed.
Figure 3:
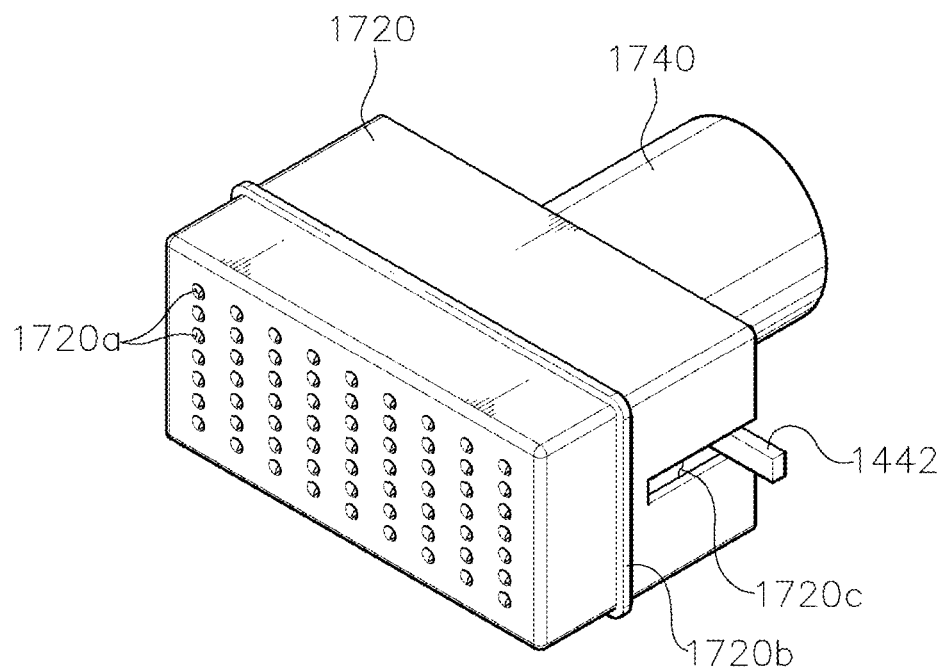
FIG. 3 is an enlarged view illustrating a state in which an internal microneedle protrudes when the contact plate illustrated in FIG. 2 is pressed.
Figure 3:
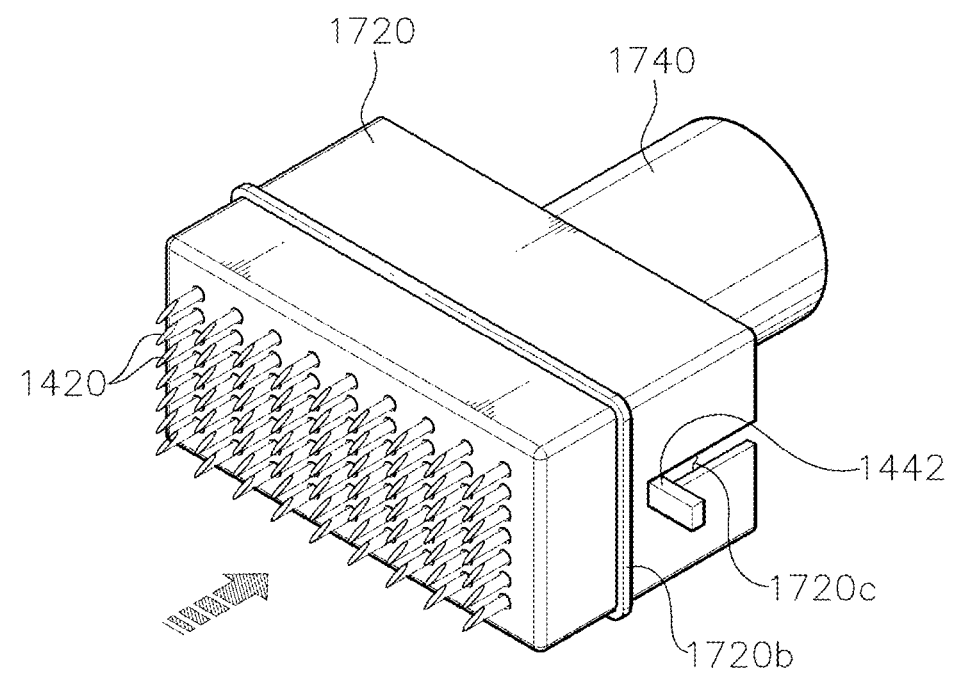

Referring to FIG. 3, a movement long groove 1720c on which a fixed end 1442 for fixing the mounting plate 1440 of the needle portion 1400 to the inside of the contact end 1140 is moved is formed on a circumferential surface of the contact member 1720, and as the fixed end 1442 provided on an outer surface of the mounting plate 1440 is moved on the movement long groove 1720c, the contact plate 1700 is slidingly moved in the contact end 1140.

Referring to FIGS. 4 and 5, a contact plate support portion 1800 for elastically supporting the contact plate 1700 is provided in the main body portion 1100, and the contact plate support portion 1800 is preferably provided in the contact end 1140 of the main body portion 1100.

The contact plate support portion 1800 includes a protrusion 1820 and a spring member 1840. The protrusion 1820 is provided in the contact end 1140 and protrudes inward from an inner circumferential surface of the contact end 1140. The spring member 1840 is provided in the contact end 1140 and has one end in close contact with an inner surface of the contact end 1140 and the other end in close contact with the contact plate 1700, and thus, the spring member 1840 elastically supports the contact plate 1700. The protrusion 1820 is located inside the spring member 1820 to fix a position of the spring member 1820.

A guide protrusion 1720b that limits a protrusion range of the contact plate 1700 protruding to the outside of the contact end 1140 is preferably provided on a circumferential surface of the contact plate 1700 that slidingly moves in the contact end 1140, and as the guide protrusion 1720b is caught on the contact end 1140, a range in which the contact plate 1700 is exposed to the outside of the contact end 1140 is limited.

Therefore, when a clinician grips the grip end 1120 and then the contact end 1140 comes into contact with the skin of the treatment subject, the contact plate 1700 is pushed to insert the plurality of microneedles 1420 into a dermis of the treatment subject such that liquid medicine and carbon dioxide may be directly injected into the dermal layer of the treatment subject without forming a linear long hole, and thus, it is possible to easily inject a certain amount of liquid medicine and carbon dioxide into the dermal layer of the treatment subject at a constant pressure by using a simple physical force without using a complex electronic device.

Although the present invention is described with reference to the embodiment illustrated in the drawings, which is a merely example, and those skilled in the art will understand that various modifications and equivalent other embodiments are possible therefrom. Therefore, the true technical protection scope of the present invention should be determined by the technical idea of the appended claims.

INDUSTRIAL APPLICABILITY

The present invention may be used in a device for injecting liquid medicine.

The invention claimed is:

1. A microneedle stamp device for injecting liquid medicine, the microneedle stamp device comprising:
   a main body portion including a grip end configured to be gripped by a clinician and a contact end configured to come into contact with a skin of a treatment subject;
   a carboxy cartridge provided in the main body portion and storing carbon dioxide to be injected into the skin of the treatment subject;
   a liquid medicine storage portion provided outside the main body portion and connected to the carboxy cartridge and storing the liquid medicine to be injected into the skin of the treatment subject together with the carbon dioxide supplied from the carboxy cartridge;
   a needle portion connected to the carboxy cartridge and the liquid medicine storage portion and configured to inject the carbon dioxide and the liquid medicine supplied from the carboxy cartridge and the liquid medicine storage portion into the skin of the treatment subject;
   a power portion provided in the grip end and configured to be operated by an external force applied from an outside of the power portion to provide pressure to the carboxy cartridge and the liquid medicine storage portion such that the carbon dioxide stored in the carboxy cartridge and the liquid medicine stored in the liquid medicine storage portion is supplied to the needle portion;
   a connection portion configured to connect the carboxy cartridge to the needle portion; and
   a contact plate provided at the contact end of the main body portion and protruding to an outside of the contact end; the contact plate including a plurality of through-holes through which the needle portion provided in the contact plate is configured to pass through; and the contact plate is configured to slidingly move to the inside of the contact end when coming into contact with the skin of the treatment subject,
   wherein, when the contact plate comes into contact with the skin of the treatment subject, the contact plate slidingly moves to the inside of the contact end to apply the external force to the power portion to operate the power portion to supply the liquid medicine and the carbon dioxide to the needle portion.

2. The microneedle stamp device of claim 1, further comprising:
   a contact plate support portion provided in the main body portion to elastically support the contact plate,
   wherein the contact plate support portion includes a protrusion provided in an inner side of the contact end and protruding inward from an inner surface of the contact end, and a spring member provided in the contact end and having one end in contact with the inner surface of the contact end and the other end in contact with the contact plate,
   wherein the protrusion is located inside the spring member, and
   wherein a guide protrusion is provided on a circumferential surface of the contact plate to guide a protrusion range of the contact plate protruding to the outside of the contact end.

3. The microneedle stamp device of claim 2, wherein
   a pressure button for operating the power portion is exposed to an outside of the power portion, and
   when the contact plate slidingly moves, the contact plate presses the pressure button to operate the power portion, and
   the power portion is formed with a connection hole through which one end of the liquid medicine storage portion passes to be connected to the carboxy cartridge.

4. The microneedle stamp device of claim 3, wherein the adhesive plate comprises:
   a contact member having a plurality of through-holes through which the needle portion passes; and
   a pressure member protruding to one side of the contact member and configured to press the pressure button while passing through a through-hole formed in the contact end when the contact plate slidingly moves.

5. The microneedle stamp device of claim 4, wherein the needle portion includes a plurality of microneedles each having one end passing through the plurality of through-holes, and a mounting plate having one side on which the other end of each of the plurality of microneedles is mounted and an opposite side on which a connection end connected to the connection portion is provided, a flow path through which the liquid medicine supplied through the connection portion and the connection end flows is formed in the mounting plate, and the liquid medicine is supplied to the plurality of microneedles through the flow path.

6. The microneedle stamp device of claim 5, wherein
   a fixed end for fixing the mounting plate to an inside of the contact end is provided on an outer surface of the mounting plate, and
   a movement long hole through which the fixed end is moved is formed in the contact member.

7. The microneedle stamp device of claim 5, wherein the plurality of microneedles have thickness of 0.25 mm to 0.8 mm and have lengths of 0.2 mm to 3 mm.

* * * * *